United States Patent
Roy et al.

(10) Patent No.: US 11,177,043 B2
(45) Date of Patent: Nov. 16, 2021

(54) SYSTEM AND METHOD TO DETERMINE THE BIOMECHANICAL DEGRADATION IN HUMAN CORNEA USING TOMOGRAPHY IMAGING

(71) Applicant: Narayana Nethralaya Foundation, Bangalore (IN)

(72) Inventors: Abhijit Sinha Roy, Bangalore (IN); Rohit Shetty, Bangalore (IN); Katkeri Bhujang Shetty, Bangalore (IN)

(73) Assignee: Narayana Nethralaya Foundation, Bangalore (IN)

( * ) Notice: Subject to any disclaimer, the term of this patent is extended or adjusted under 35 U.S.C. 154(b) by 72 days.

(21) Appl. No.: 16/486,709

(22) PCT Filed: Mar. 14, 2018

(86) PCT No.: PCT/IB2018/051716
§ 371 (c)(1),
(2) Date: Aug. 16, 2019

(87) PCT Pub. No.: WO2018/167696
PCT Pub. Date: Sep. 20, 2018

(65) Prior Publication Data
US 2020/0013514 A1 Jan. 9, 2020

(30) Foreign Application Priority Data
Mar. 14, 2017 (IN) .............................. 201741008796

(51) Int. Cl.
*G16H 50/50* (2018.01)
*A61B 3/107* (2006.01)
(Continued)

(52) U.S. Cl.
CPC .......... *G16H 50/50* (2018.01); *A61B 3/0025* (2013.01); *A61B 3/107* (2013.01); *A61B 6/03* (2013.01);
(Continued)

(58) Field of Classification Search
None
See application file for complete search history.

(56) References Cited

U.S. PATENT DOCUMENTS

| | | | |
|---|---|---|---|
| 2014/0114145 A1* | 4/2014 | Wang | A61B 3/107 600/301 |
| 2018/0000342 A1* | 1/2018 | Tang | G06T 7/0014 |
| 2020/0013514 A1* | 1/2020 | Roy | G16H 50/50 |

OTHER PUBLICATIONS

Kling S, Bekesi N, Dorronsoro C, Pascual D, Marcos S (2014) Corneal Viscoelastic Properties from Finite-Element Analysis of In Vivo Air-Puff Deformation. PLoS ONE 9(8): e104904. doi: 10.1371/journal.pone.0104904 (Year: 2014).*

* cited by examiner

Primary Examiner — Tahmina N Ansari
(74) Attorney, Agent, or Firm — David G. Rosenbaum; Rosenbaum IP, P.C.

(57) ABSTRACT

The invention relates to a system and method of implementation of artificial intelligence and tomography imaging to determine the biomechanical degradation or degeneration in human cornea. The invention relates to a combination tool using artificial intelligence and tomography imaging to map the region of degeneration in the cornea. The method of artificial intelligence and corneal tomography imaging includes analysis of changes in the structure of the cornea, constructing the 3D volumes using corneal tomography, meshing the 3D volumes with the elements for biomechanical simulations by using finite element modules, application of artificial intelligence to determine the region of biome-
(Continued)

chanical degeneration in cornea. The combination tool of the invention is effective in predicting the progression of the disease by analyzing the chronic steepening of the cornea by quantitating the parameters such as increase in curvature, aberrations of the cornea.

9 Claims, 6 Drawing Sheets

(51) Int. Cl.
  *G06T 7/00* (2017.01)
  *A61B 3/00* (2006.01)
  *A61B 6/03* (2006.01)
  *A61B 8/10* (2006.01)
(52) U.S. Cl.
  CPC .............. *A61B 8/10* (2013.01); *G06T 7/0014* (2013.01); *G06T 2207/10081* (2013.01); *G06T 2207/10132* (2013.01); *G06T 2207/30041* (2013.01)

SYSTEM AND METHOD TO DETERMINE THE BIOMECHANICAL DEGRADATION IN HUMAN CORNEA USING TOMOGRAPHY IMAGING

CROSS-REFERENCE TO RELATED APPLICATIONS

The present application is a national phase application and claims priority to PCT application serial no. PCT/IB2018/051716, filed Mar. 14, 2018, which claims priority to Indian Patent application serial no. IN 201741008796, filed Mar. 14, 2017, each herein incorporated by reference in their entireties.

TECHNICAL FIELD OF THE INVENTION

The present invention relates to implementation of artificial intelligence and tomography imaging to determine the biomechanical degradation or degeneration in human cornea. The invention relates to a combination tool using artificial intelligence and tomography imaging to determine the degradation of cornea. The invention also discloses a method of determining the extent of biomechanical degradation in human cornea.

BACKGROUND OF THE INVENTION

Cornea is a transparent anterior part of the eye that covers the iris, pupil and anterior chamber. Cornea has unmyelinated nerve endings that are sensitive to touch, temperature and chemicals. Usually, cornea does not have blood vessels, instead, oxygen dissolves in tears and then diffuses throughout the cornea to keep it healthy. Similarly, nutrients are transported via diffusion from the tear fluid through outside surface and the aqueous humor through the inside surface and also from neurotrophins supplied by nerve fibres that innervate it.

In human eye, cornea has a diameter of about 11.5 mm and a thickness of 0.5-0.6 mm in the center and 0.6-0.8 mm at the periphery. Cornea is responsible for about 70 percent of the eye's focusing power. The characteristics such as transparency, a vascularity and the presence of immature resident immune cells and immunologic privilege make cornea a very special tissue.

Corneal degradation or degeneration results in several disorders such as keratoconus, pellucid marginal degeneration, where cornea undergoes physical changes. These changes may be inflammatory, structural and biomechanical in nature. It is observed that in these disorders, there is severe thinning of the corneal layer and biomechanical degradation of the cornea. The diseases are progressive in nature, which implies that the severity of the disease increases over time, if left undiagnosed or unmanaged. The progression of the disease results in chronic steepening of the cornea resulting in increase in curvature, corneal aberrations and wave front aberrations.

In order to analyze the progression of the disease, there is requirement of a specific tool to predict the changes in the corneal surface specifically to determine the regions of degradation. These changes are measured using clinical topography and tomography devices. Corneal tomography is a non-invasive medical imaging technique for mapping the surface curvature of the cornea. It is a computer assisted diagnostic tool that creates a three-dimensional map of the surface curvature of the cornea. Corneal tomography is of critical importance in determining the quality of vision and corneal health.

Corneal tomography is used to identify the curvature of the cornea and to identify distortions such as keratoconus, scarring of the cornea or other distortions. It is also used as an aid in fitting contact lenses and in the evaluation of patients undergoing eye surgeries.

The greatest advantage of corneal tomography is its ability to detect irregular conditions that are usually invisible to conventional testing methods. Corneal tomography produces a detailed, visual description of the shape and power of the cornea, which provides the details regarding the condition of the corneal surface. These details are used to diagnose, monitor and to treat various eye conditions. They are also used in fitting contact lenses and for planning surgery, including laser vision correction.

The U.S. application Ser. No. 09/565,851 titled "Systems and methods for imaging corneal profiles" discloses systems, methods and apparatus for generating images of portions of the patient's eye such as the anterior surface of the cornea. The methods and apparatus of the present invention are particularly useful for directly imaging the profile of the ablated region of the cornea. These methods and apparatus are helpful to image the exterior edge of the eye to characterize the profile of ablated corneas and to determine the spatial variance of tissue ablation rates during the surgical procedures. The methods and apparatus also provide provisions for generating one or more images depicting the profile of the ablated region of the cornea. The profile is registered with a pre-ablation profile to provide feedback regarding the true ablation properties of the eye. This feedback permits the laser system to be programmed with a laser ablation algorithm based on the measured ablation properties of the eye. However, the tool is silent with respect to the specific region as a target for intervention.

The U.S. application Ser. No. 07/931,271 titled "Method and apparatus for imaging and analysis of corneal tissue" discloses a method and apparatus for in vivo imaging of corneal tissue. In general, the method comprises providing a laser beam having a substantially planer configuration. The substantially planar laser beam is directed through a cross-sectional portion of the cornea of a patient, so as to illuminate the cross-sectional portion and cause the laser beam to be scattered by molecules in the corneal tissue. Then, at least a portion of the scattered laser light is detected so as to form a cross-sectional image of the corneal tissue. In general, the planar configured laser beam exhibits a slit-like cross-sectional dimension having essentially the same width dimension over the depth of field within which the largest depth dimension of the eye extends. These unique characteristics of the illumination beam permit the formation of clear, in-focus images detected at the image detection plane. The method and apparatus of the invention are utilized to produce in-focus cross-sectional images from which the optical density of corneal tissue is precisely measured. The method and apparatus of the invention are useful for objectively measuring the optical density of corneal tissue as well as precisely measuring the physical dimensions such as thickness and curvature of the cornea and its correct spatial relationship within the eye. However, the invention is silent with respect to the imaging on complete corneal tissue and to quantitate the extent of distortions of cornea in order to identify the progression of the disease.

The existing methods or tools of tomography are useful in identifying the distortions in the corneal tissue. However, the available methods are not useful for quantitative measurement and to identify the specific regions of biomechanical degradation. The degradation of the corneal tissue may be due to inflammatory, structural or biomechanical changes. It is crucial to analyze the biomechanical changes in the corneal tissue by the existing methods or apparatus.

Hence, there is a requirement of the combination tool to analyze the biomechanical degradation of the corneal tissue. The analysis and biomechanical degradation of the corneal tissue also helps in analyzing the progression of the disease. There is a requirement of a tool that analyzes the specific region as target for intervention such as transplant and corneal crosslinking.

SUMMARY OF THE INVENTION

The invention provides a system with a combination of artificial intelligence and corneal tomography to determine the regions of degradation in human cornea. The system comprises corneal tomography, finite element simulation module and artificial intelligence module. Corneal tomography helps in analyzing the anterior and posterior corneal surfaces with elevation and curvature and in reconstruction of 3D (Dimensional) or 2D surface of the cornea. Corneal tomography also provides elevation data of the corneal surface and layers in terms of point cloud. These surfaces are useful to create 3D volumes that are meshed with elements for biomechanical simulations. The imaging tool further comprises finite element simulation module. The 3D volumes constructed using corneal tomography is populated with biomechanical properties of the cornea. The finite element simulations help in computing the deformations. Finite element simulation module also utilizes ray tracing for computing aberrations. The artificial intelligence module uses longitudinal tomography maps of the same eye or a single cross-section tomography of the patient eye referenced to a normative database of corneal shape to determine the region of biomechanical degeneration.

The invention also discloses a method of implementing artificial intelligence and corneal tomography in combination to analyze the corneal tomography of the patient and use biomechanical simulation with finite element modeling to determine the region of degradation in human cornea.

The analysis of physical changes in cornea helps in analyzing the severity of the disease and acts a marker for progression of the disease. The method disclosed in the invention helps in analyzing the corneal diseases. The method of artificial intelligence and corneal tomography imaging includes analysis of changes in the structure of the cornea, constructing the 3D volumes using corneal tomography, meshing the 3D volumes with the elements for biomechanical simulations by using finite element modules, application of artificial intelligence to determine the region of biomechanical degeneration in cornea. The tool compares corneal tomography at different follow-up visits of the patient and use biomechanical simulation with finite element modeling to determine the region of degradation by analyzing the spatial area and location of the disease.

The invention helps in analyzing the axial curvature before treatment with keratoconic pattern. The treatment results in change of the axial curvature from the keratoconic to astigmatism pattern and the difference in the axial curvature post treatment is illustrated. The system and method of combination of artificial intelligence and tomography imaging is useful in determining the biomechanical degradation in human cornea. The combination tool of the invention is effective in predicting the progression of the disease by analyzing the chronic steepening of the cornea by quantitating the parameters such as increase in curvature, aberrations of the cornea.

BRIEF DESCRIPTION OF DRAWINGS

In the accompanying figures, like elements are identified by like reference numerals among the several preferred embodiments of the present invention.

DETAILED DESCRIPTION OF THE INVENTION

Figure 1:
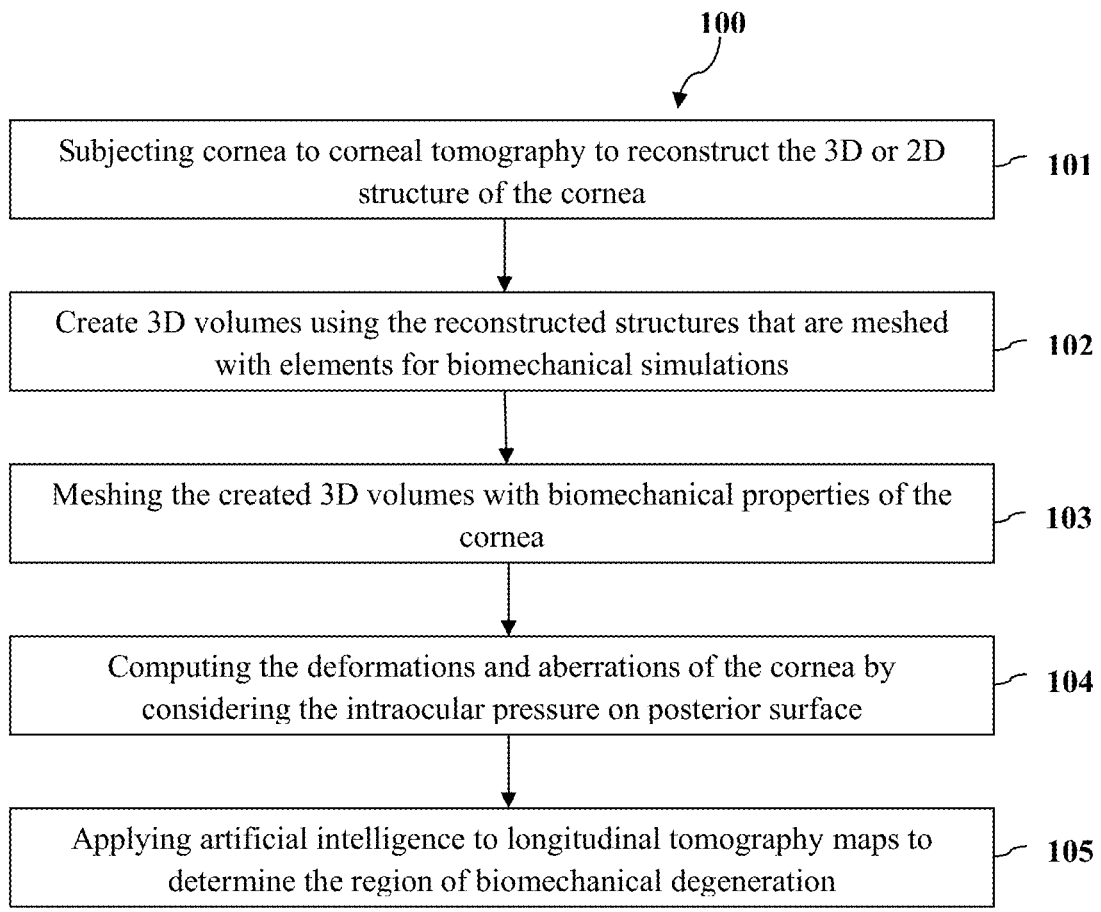
FIG. 1 illustrates the method of imaging the cornea using the combination tool.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the software, electrical, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The term "Corneal Tomography" refers to a technique for displaying a representation of a cross section of a cornea using X-rays or ultrasound.

The term "Artificial Intelligence" refers to the development of computer systems that are capable of performing tasks normally requiring human intelligence such as visual perception, speech recognition, decision-making, and translation between languages.

The invention provides a system with a combination of artificial intelligence and corneal tomography to determine the regions of degradation in human cornea. The system is an automated tool, which is the combination of artificial intelligence and corneal tomography. The system comprises corneal tomography, finite element simulation module and artificial intelligence module.

The invention also discloses a method of implementing artificial intelligence and corneal tomography in combination to analyze the corneal tomography of the patient and use biomechanical simulation with finite element modeling to determine the region of degradation in human cornea.

Corneal tomography is a non-invasive medical imaging technique for mapping the surface curvature of the cornea, which helps in the assessment of the corneal shape. The technique of corneal tomography helps in analyzing the anterior and posterior corneal surfaces with elevation and curvature. Corneal tomography helps in reconstruction of 3D (Dimensional) or 2D surface of the cornea. Corneal tomography provides elevation data of the corneal surface and layers in terms of point cloud. These surfaces are useful to create 3D volumes that are meshed with elements for biomechanical simulations.

The tool also comprises finite element simulation module. The 3D volumes, constructed using corneal tomography, are populated with biomechanical properties of the cornea. The finite element simulations help in computing the deformations. Finite element simulation module also utilizes ray tracing for computing aberrations. Since the finite element model is generally built for normal corneas, modifications to the material model are implemented to model disease related changes. Further, finite element models include fiber dependent hyperplastic material models.

The combination tool further comprises the artificial intelligence module, which uses longitudinal tomography maps of the same eye or a single cross-section tomography of the patient eye referenced to a normative database of corneal shape to determine the region of biomechanical degeneration.

The invention further includes the method of implementation of artificial intelligence and corneal tomography imaging to determine the regions of biomechanical degradation in cornea.

Cornea exhibits physical changes such as inflammatory, structural and biomechanical changes, which leads to degeneration or degradation of the corneal tissue leading to several corneal diseases such as keratoconus, pellucid marginal degeneration etc. The analysis of such physical changes helps in analyzing the severity of the disease and acts a marker for progression of the disease. The method disclosed in the invention helps in analyzing the corneal diseases.

The method of artificial intelligence and corneal tomography imaging includes analysis of changes in the structure of the cornea, constructing the 3D volumes using corneal tomography, meshing the 3D volumes with the elements for biomechanical simulations by using finite element modules, application of artificial intelligence to determine the region of biomechanical degeneration in cornea.

FIG. 1 illustrates the method of imaging the cornea using the combination tool. The cornea is imaged using a combination tool comprising corneal tomography, finite element simulation module and artificial intelligence module. The method (100) of imaging starts with step (101) of subjecting the cornea to corneal tomography to reconstruct the 3D or 2D structure of the cornea. The 3D structures are constructed by obtaining the elevation data of the corneal surface and layers in terms of point cloud. These point clouds are easily reconstructed using commercial 3D computer aided drafting packages or other open source tools. At step (102), the reconstructed structures are used to create 3D volumes that are meshed with elements for biomechanical simulations. At step (103), the 3D volumes created are meshed with biomechanical properties of the cornea. The biomechanical properties determine the fiber dependent, anisotropic, hyperelastic behavior of the cornea. At step (104), the deformations of the cornea are computed by considering the intraocular pressure as the mechanical load on the posterior surface of the cornea and aberrations are computed by analyzing the change in curvature and surface wave front of the cornea. Ray tracing is also used for computing aberrations. At step (105), artificial intelligence is applied to longitudinal tomography maps to determine the region of biomechanical degeneration. The artificial intelligence determines the region of biomechanical degeneration in the cornea as function of 3-D coordinates. The different metrics such as area, perimeter and volume of the degenerate zone within the cornea are calculated to analyze the biomechanical degradation.

The tool compares corneal tomography at different follow-up visits of the patient and use biomechanical simulation with finite element modeling to determine the region of degradation by analyzing the spatial area and location of the disease. Corneal tomography is either anterior surface curvatures and aberrations, and/or the same of sub-epithelium corneal layers such as the Bowman's surface. In case where patients' follow-up visits are not available, the regions of the degeneration are determined from a general database of normal patient tomography.

Since the finite element model is generally built for normal corneas, modifications to the material model are implemented to model disease related changes. Most of the degenerations lead to loss of collagen, the material model properties of the disease eyes are considered to be a fraction between 0 and 1 of the same for normal corneas. Thus, 0 indicates total loss of biomechanical strength and 1 indicates no loss.

In order to determine the regions of biomechanical degeneration, the artificial intelligence module uses longitudinal tomography maps of the same eye or a single cross-section tomography of the eye referenced to a normative database of corneal shape. In case of use of longitudinal tomography maps of the same eye, artificial intelligence compares the corneal curvature and aberrations between the normal state before the onset of progression and the state where the eye has progressed to the disease. Since the assumption that disease is caused by biomechanical weakness, the artificial intelligence modulates the material properties in the finite element model to derive the diseased shape of the cornea. In case of use of single cross-section tomography of the eye referenced to a normative database of corneal shape, the artificial intelligence compares the corneal curvature and aberrations between the normal state of an age matched eye with curvature and thickness representative of the population and the state where the eye has progressed to the disease. Further, in both the cases, the modulations are achieved by implementing optimization routines such as Nelder-Mead search, Levenberg-Marquedt gradient method. The artificial intelligence determines spatial map of region of biomechanical degeneration in the diseased state of the cornea. The optimization algorithms minimize the difference between the predicted curvature from finite element simulations and the measured curvature from cornea in the progressed state of the disease. This is an iterative process and continues till the difference becomes smaller than a predefined tolerance.

Figure 2:
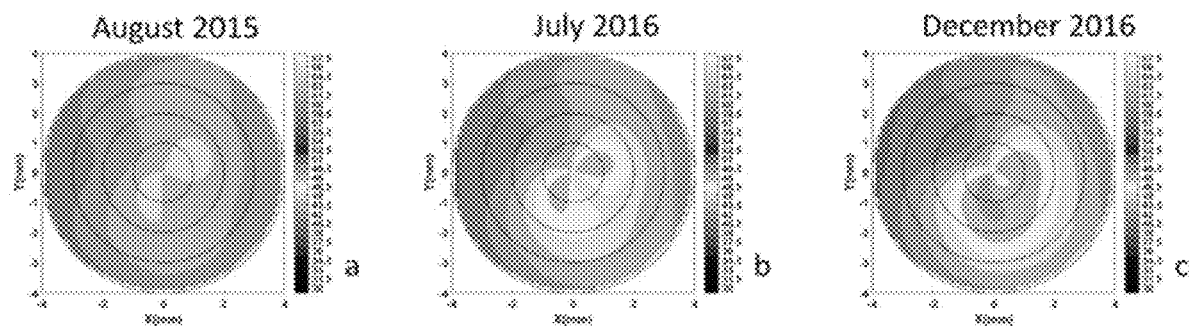
FIG. 2 illustrates the axial curvature of a patient cornea measures during different timelines.

FIG. 2 illustrates the axial curvature of a patient cornea measures during different timelines. The axial curvature of the cornea is measured using corneal tomography during different time periods. The result shows the steeping of the cornea with time. FIGS. 2a, 2b and 2c illustrates the axial curvature of cornea in August 2015, July 2016 and December 2016 respectively indicating the steeping of the cornea evidencing the progression of the disease with time.

FIG. 3 illustrates the predicted curvature of the cornea at the same time points using the artificial intelligence.

Figure 3A:
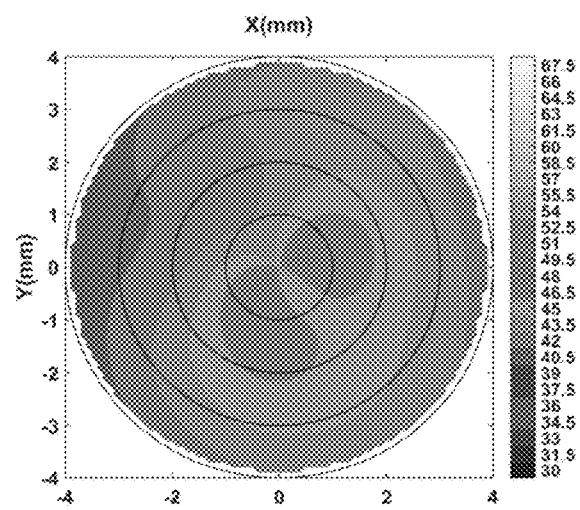
FIG. 3 illustrates the predicted curvature of cornea at the same time points.
Figure 3B:
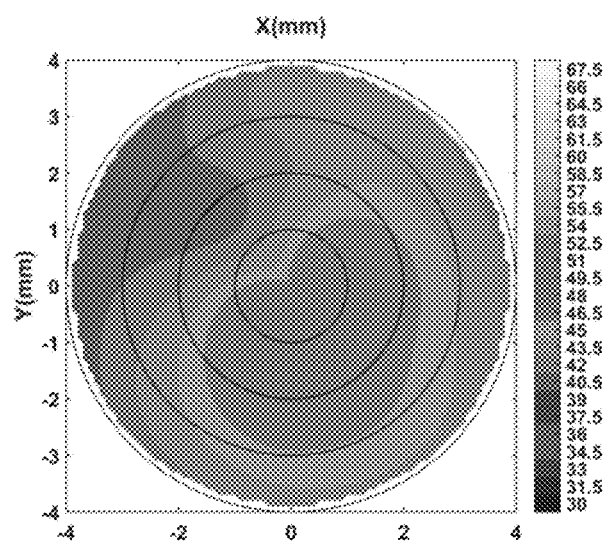

FIG. 3a and FIG. 3b indicate the degeneration of cornea.

Figure 3C:
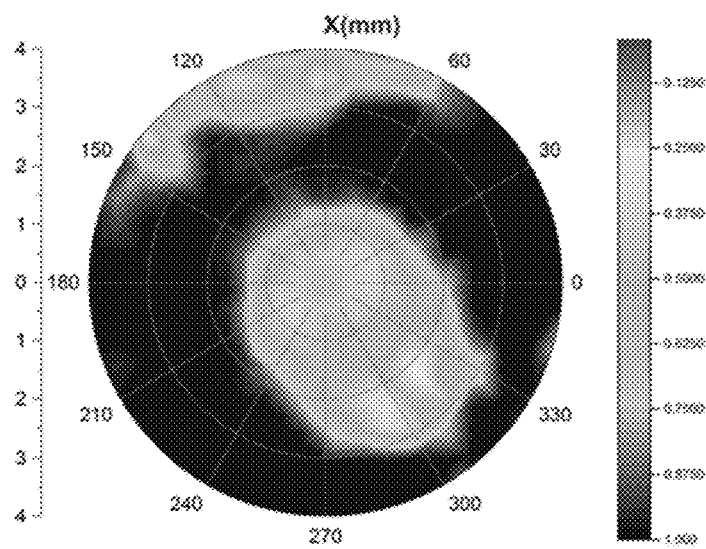
Figure 3D:
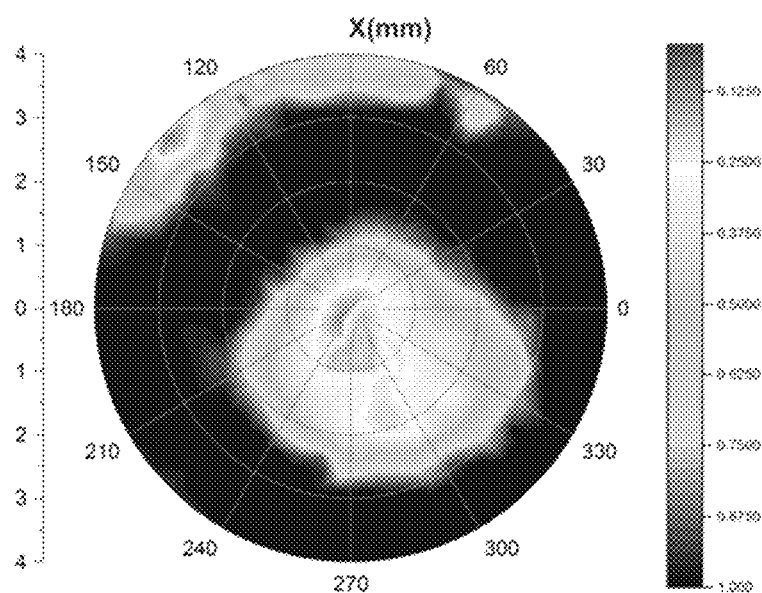

FIG. 3c and FIG. 3d indicate the corresponding regions of cornea with biomechanical degeneration in July 2016 and December 2016, respectively. The magnitude of the material properties in the degenerate zone is lower than the magnitude of the same in the non-degenerate zone. Further, the size of the degenerate zone increased from July 2016 to December 2016 due to progression of the disease. The same cornea is treated with corneal crosslinking by treating only the degenerate zone as predicted by the artificial intelligence.

FIG. 4 illustrates the axial curvature of the cornea before and after treatment.

Figure 4A:
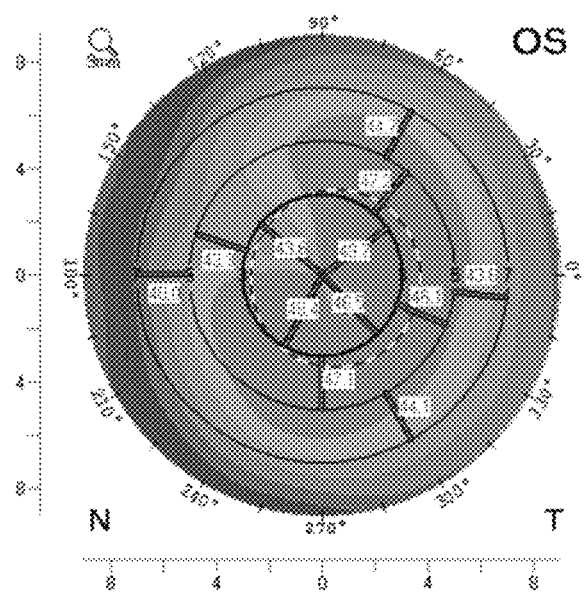
FIG. 4 illustrates the axial curvature of the cornea before and after treatment.

FIG. 4a illustrates the axial curvature after treatment with a regular astigmatism pattern.

Figure 4B:
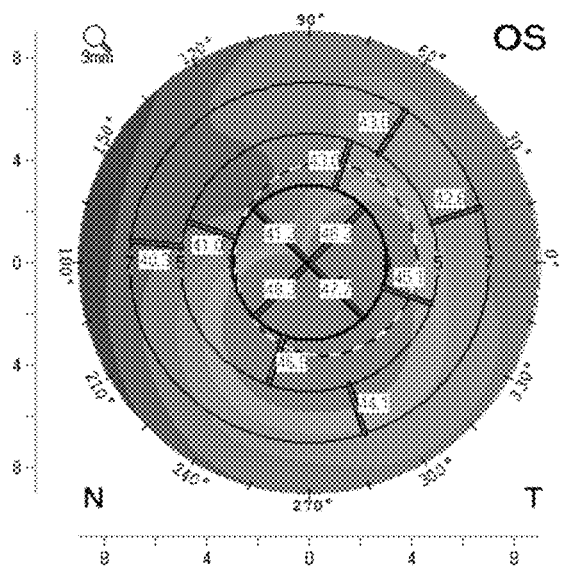

FIG. 4b illustrates the axial curvature before treatment with keratoconic pattern. The treatment results in change of the axial curvature from the keratoconic to astigmatism pattern and the difference in the axial curvature post treatment is illustrated.

Figure 4C:
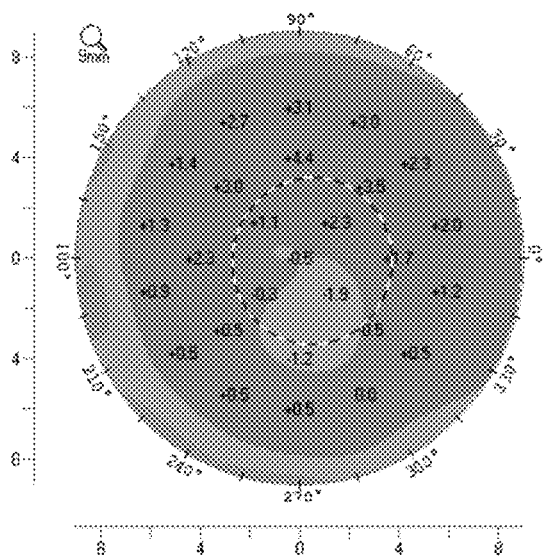

FIG. 4c highlights the region of profound flattening indicating a decrease of −2D surrounded by an annular zone of sharp steepening in excess of +4D.

Figure 5:
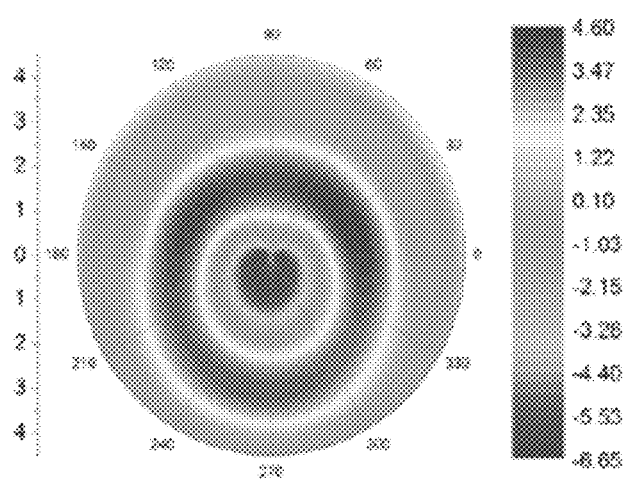
FIG. 5 illustrates the consistency of axial curvature of the cornea as predicted by theoretical biomechanical simulation models.

FIG. 5 illustrates the consistency of axial curvature of the cornea as predicted by theoretical biomechanical simulation models. The observations from FIG. 4 are in consistent with the theoretical simulations of outcomes of corneal crosslinking in corneas of patients by treating only the degenerate zone as illustrated in FIG. 5.

The system and method of combination of artificial intelligence and tomography imaging is useful in determining the biomechanical degradation or degeneration in human cornea. The combination tool of the invention is effective in predicting the progression of the disease by analyzing the chronic steepening of the cornea by quantitating the parameters such as increase in curvature, aberrations of the cornea. The tool compares corneal tomography at different time periods and use biomechanical simulation with finite element modeling to determine the region of degradation by analyzing the spatial area and location of the disease.

As used in this application, the term "system" is intended to refer to a computer-related entity, either hardware, a combination of hardware and software, software, or software in execution. For example, a component of the system can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data.

Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

We claim:

1. A system to determine one or more regions of biomechanical degradation of human cornea, the system comprises:
   a. a corneal tomography is configured to map the surface curvature of cornea;
   b. a finite element simulation module for computing one or more deformations in cornea; and
   c. an artificial intelligence module for determining one or more regions of biomechanical degeneration in cornea.

2. The system as claimed in claim 1, wherein the corneal tomography is configured to analyse the anterior and posterior corneal surfaces with elevation and curvature to reconstruct 3D (Dimensional) or 2D structure of the cornea.

3. The system as claimed in claim 1, wherein the finite element simulation module for utilizing ray tracing for one or more computing aberrations after populating with biomechanical properties of the cornea.

4. The system as claimed in claim 1, wherein the artificial intelligence module for determining biomechanical degeneration by using longitudinal tomography maps of the same eye or a single cross-section tomography of the eye referenced to a normative database of corneal shape.

5. A method to determine one or more regions of biomechanical degradation of human cornea, the method comprises the steps of:
   a. subjecting cornea to corneal tomography for reconstructing the 3D or 2D structure of cornea;
   b. creating one or more 3D volumes using the reconstructed structures;
   c. meshing the created 3D volumes with biomechanical properties of the cornea;
   d. computing one or more deformations of the cornea by considering the intraocular pressure as the mechanical load on the posterior surface of the cornea and one or more aberrations by analysing the change in curvature and surface wave front of the cornea; and
   e. applying artificial intelligence to longitudinal tomography maps to determine the region of biomechanical degeneration.

6. The method as claimed in claim 5, wherein the 3D structures of cornea are constructed by obtaining the elevation data of the corneal surface and layers in terms of point cloud.

7. The method as claimed in claim 5, wherein the biomechanical properties determine the fiber dependent, anisotropic, hyper elastic behavior of the cornea.

8. The method as claimed in claim 5, wherein the artificial intelligence determines the region of biomechanical degeneration as function of 3-D coordinates by analysing metrics such as area, perimeter and volume of the degenerate zone within the cornea.

9. The method as claimed in claim 5, wherein the method predicts the progression of the disease by analyzing the chronic steepening of cornea by quantitating the parameters such as increase in curvature and aberrations of cornea.

* * * * *